United States Patent
Jackson et al.

(10) Patent No.: US 6,403,576 B1
(45) Date of Patent: Jun. 11, 2002

(54) ANTIFUNGAL AND ANTIPARASITIC COMPOUNDS

(75) Inventors: Joan E. Jackson, Rockville; Maurice M. Iwu; Christopher O. Okunji, both of Silver Spring, all of MD (US); Cyrus Bacchi, East North Port, NY (US); John D. Talley, Jr., Washington, DC (US); Johnson F. Ayafor, Dechang (CM)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/382,128

(22) Filed: Aug. 24, 1999

Related U.S. Application Data
(60) Provisional application No. 60/097,672, filed on Aug. 24, 1998.

(51) Int. Cl.$^7$ .............. A61K 31/55; A61K 39/00; A01N 25/00; A01N 25/34
(52) U.S. Cl. .............. 514/211; 514/211; 424/405; 424/408; 424/265.1; 424/269.1
(58) Field of Search ............ 514/211; 424/405, 424/408, 265.1, 269.1

(56) References Cited

U.S. PATENT DOCUMENTS

| | | | | |
|---|---|---|---|---|
| 5,770,594 A | * | 6/1998 | Hamanaka et al. | |
| 5,831,115 A | * | 11/1998 | Arendsen et al. | 560/41 |
| 5,965,553 A | * | 10/1999 | Bell et al. | 514/211 |
| 6,034,275 A | * | 3/2000 | Aebi et al. | 564/324 |

* cited by examiner

*Primary Examiner*—Frederick Krass
*Assistant Examiner*—Donna Jagoe
(74) *Attorney, Agent, or Firm*—Elizabeth Arwine; Charles H. Harris

(57) ABSTRACT

Novel antiparasitic and antifungal compositions are disclosed. The antiparasitic and antifungal compositions are useful for human and veterinary therapy for the treatment and/or prevention of parasitic infection. Also disclosed are novel mechanisms of identifying antifungal and antiparasitic compositions by their biochemical action on lipid synthesis and/or metabolism and/or excretion.

18 Claims, 1 Drawing Sheet

ANTIFUNGAL AND ANTIPARASITIC COMPOUNDS

This application claims benefit of Provisional No. 60/097,672 filed May 24, 1998.

FIELD OF THE INVENTION

Compounds are described which represent novel, efficacious, and less toxic alternatives to current antiparasitic/antifungal treatments. Compounds having action via the biochemical mechanism of inhibition of lipid synthesis and/or metabolism and/or excretion, either by direct or indirect inhibition, will have either singly or in combination antiparasite/antifungal activity. Such compounds, in most cases, are not chemically related by structure or chemical class to each other. The compounds are identified as antiparasitics and/or antifungals based on mechanism of physiologic action. Data supporting "novel use" as antiparasite/antifungal compounds are given. Many compounds herein described are FDA-approved and marketed for human use for nonparasitic/nonfungal indications. Thus, the human pharmacokinetics for oral absorption, elimination rates/mechanisms, and dose-related toxicity are known.

INTRODUCTION

Status of Leishmaniasis, trypanosomiasis, and trichomoniasis

Current drugs most frequently used to treat leishmaniasis all require parenteral administration, date back 40→50 years, and all have such severe side-effects that treatment only in a hospital setting is recommended (Bryceson, 1968, *East African Med J* 45, 110–117; Bryceson, A., 1987, *The Leishmaniases in Biology and Medicine, Vol II Clinical Aspects and Control*, Academic Press, New York, pp. 847–907). No antileishmanial is Food and Drug Administration (FDA) approved and there is no chemoprophylaxis for any leishmanial disease. Topical treatment for leishmanial disease is not effective even for cutaneous disease forms because leishmaniasis is a systemic disease (Neva, et al., 1997, *Trans R Soc Trop Med Hyg* 91, 473–475). There is no general vaccine for leishmaniases, although a live vaccine is used in the Middle East for certain Leishmania (Leishmania) tropica/Leishmania (Leishmania) major to prevent facial scarring. Drug resistance is so severe in certain endemic regions that thousands are dying in India of untreatable, multidrug resistant visceral leishmaniasis; and in Northern Africa as a result of malnutrition exacerbated disease (Cerf, et al., 1987, *J Inf Dis* 156, 1030–1033; de Beer, et al., 1991, *Am J Trop Med Hyg* 44, 283–289; Sundar, 1997, *Acta Parasitol Turicica* 21, suppl 1, 128).

Immunodeficiency, either as the result of leishmanial tubercular- or HIV coinfections, poses serious therapeutic difficulties as leishmanial coinfection is reported to potentiate the pathology of both these bacterial and viral infections (Alvar, et al., 1997, *Clin Microbiol Rev* 10, 298–319; Bernier R, et al., 1995, *J Virol* 69, 7282–7285; Bryceson, 1987, supra; Faraut-Gamarelli, et. al., 1997, *Antimicrob Agents Chemother* 41, 827–830). Global travel and commerce result in patients having complex disease exposure history, and transportation of leishmanial parasites far from their anticipated endemic regions making both diagnosis and patient management difficult (Albrecht, et al., 1996, *Arch Pathol Lab Med* 120, 189–198). Leishmaniases have an annual incidence of 2–3 million new cases per year with 12 million infected and 350 million at risk in 88 countries worldwide (Croft, 1988, *Trends Pharmacol Sci* 9, 376–381; World Report on Tropical Diseases, 1990). The need for a orally administered antileishmanial of low toxicity is critical.

Two major groups of diseases caused by flagellate protozoa are African sleeping sickness (*Trypanosoma brucei* spp.) and trichomoniasis (Trichomonas/Tritrichomonas) exhibited as *trichomoniasis vaginalis* and trichomoniasis foetus.

African trypanosomiasis affects both domestic and wild animals as well as humans in mainly rural settings (Kuzoe, 1993, *Acta Tropica* 54, 153–162; World Health Organization (WHO), 1995, *Tropical Disease Research*, Twelfth Programme Report, Geneva Switzerland) while trichomoniasis is a cosmopolitan disease in men as well as women, and a threat to cattle breeding in most agricultural areas of the world (Hammill, 1989, *Obstet Gynecol Clin North Am* 16, 531–540; Levine, 1985, *Veterinary Protozoology.* Iowa State Univ. Press, Ames, pp 59–79). Treatment of the organisms causing these diseases presents problems, in part, due to the toxicity of existing agents, and the development of resistance to existing drugs (Kuzoe, 1993, supra; Lossick, 1989, *Trichomonads Parasite in Humans.* Springer-Verlag, New York, pp 324–341).

African trypanosomiasis is endemic in over 10 million square kilometers of sub-Saharan Africa, affecting humans and all domesticated livestock (WHO, 1995, supra). There are an estimated 25,000 new cases of human disease yearly and an animal incidence of 250–300,000 cases but these estimates are low, based on recent civil unrest and lapses in local tsetse fly control and medical surveillance (WHO, 1995, supra). The primary drugs for human and veterinary trypanosomiasis have been in use for >50 years. Resistance is spreading, especially to the only available agent for late stage central nervous system (CNS) human disease, melarsoprol (van Nieuwenhove, 1992, *Ann Soc Belg Med Trop* 72, 39–51; Kuzoe, 1993, supra). Melarsoprol is also toxic, with a 3–5% incidence of cerebral episodes reported (Pepin and Milord 1994, *Adv Parasitol* 33, 2–47; Wery, 1994, *Int J Antimicrob Agents* 4, 227–238). Veterinary trypanocides include diminazene (Berenil®) and isometamidium (Samorin®) which are used prophylactically for control of disease in cattle herds (WHO, 1995, supra; Kaminsky et al., 1993, Acta Tropica 54, 19–30). Resistance to both agents has been documented in field studies (Kuzoe, 1993, supra; Schoenfeld et al., 1987, *Trop Med Parasitol* 38, 117–180; Williamson, 1970, *The African Typanosomiases.* Allen & Unwin, London, pp 125–224). For these reasons, there is an urgent need to develop new trypanocides.

*Trichomonas vaginalis* is one of the most prevalent sexually transmitted pathogen of the human urogenital tract. It infects the vaginal epithelium, causing severe irritation and the development of a discharge. In addition to social distress caused by the disease, recent evidence suggests a high incidence rate between cervical cancer and trichomoniasis (Gram et al., 1992, *Cancer Causes and Control* 3, 231–236). The disease is widespread, with about 3 million cases in women annually in the United States alone (Hammill, 1989, supra). Chemotherapy for human trichomoniasis relies on a group of 5'-nitroimidazoles, with metronidazole (Flagyl®) being the most utilized. In the United States, metronidazole is the only available agent, although other derivatives are used in Europe and other areas. Since metronidazole has been in continuous use since 1955, there has been increasing reports of metronidazole-resistant vaginitis (Meingassner & Thurner, 1979, *Antimicrob Agents Chemother* 15, 254–258; Wong et al., 1990, *Australia-New Zealand J Obstet Gynecol*

30, 169–171; Voolman & Boreham, 1993, *Med J Australia* 159, 490). Because of its potential to produce free radicals upon reduction, it is potentially mutagenic and not given to pregnant women (Lossick, 1989, supra). At present, there is no alternative to the 5'-nitroimidazoles for therapy of metronidazole-refractory disease, nor for treatment of pregnant women.

*Trichomonas* foetus is the agent of bovine trichomoniasis, causing reproductive failure. Parasites are spread by infected bulls, multiply in the vagina and invade the cervix and uterus. One to 16 weeks after breeding, abortion of the fetus occurs (Levine, 1985, supra). If the placenta and fetal membranes are eliminated following abortion, the cow may spontaneously recover. If some of these tissues remain inside the animals, permanent sterility may result. There is no satisfactory treatment for diseased cows, while treatment of bulls is tedious and expensive. Aminoquinuride (Surfen®) or acriflavine (Trypaflavine®) may be used topically, with dimetridazole injected into the urethra. Unless the bull is valuable, it is usually destroyed (Levine, 1985, supra). The disease is common in open range breeding ranches and may reach epidemic levels. In Australia, 40–65% of cattle were reported to be infected, while the prevalence in California was reported to be 14% (Yule et al., 1989, *Parasitol Today* 5, 373–377). The economic losses due to bovine trichomoniasis have been estimated to be $665/infected dairy cow, while the widespread prevalence of the disease would account for tens of millions of dollars annually (Yule et al., 1989, *Parasitol Today* 5, 373–377). The overall situation for chemotherapy of trichomoniasis therefore, is the reliance on a single drug as drug class for chemotherapy of human disease, and no effective control measures for bovine trichomoniasis.

SUMMARY OF THE INVENTION

Preliminary evidence from our ethnomedical and ethnobotanical drug discovery research as well as background literature describing different aspects of the parasite's sterol pathway and cholesterol requirements and importance to parasite survival, has led to the discovery of compounds chosen on the basis of their physiological function on different parts of the sterol synthesis, and/or excretion, and/or metabolism which offer potential chemotherapeutic target(s) having low toxic potential for man. Several of these compounds have been tested for their antiparasitic/antifungal activity as described in the Examples.

The following is a brief summary of the background and data which led to the discovery of the antiparasitic/antifungal compounds of the present invention.

Lipids comprise up to 15% of the total dry weight of Leishmania spp. (Meyer and Holz, 1966, *J Biol Chem* 241, 5000–5007; Beach, et al., 1979, *J Parasitol* 65, 203–216; Fish, et al., 1981, *Mol Biochem Parasitol* 3, 103–116). Lipid metabolism is critical to parasite membrane transport, cell replication, and, therefore, to survival. The lipid metabolism of Leishmania spp. including precursors, synthetic pathways, regulator molecules, and end products for membrane fatty acids, lipids, and sterols is known to mimic parts of fungal, bacterial-, plant-, and human lipid pathways, while completely duplicating none. Because leishmanial lipid metabolism is unique among organisms, genetically conserved (Wendt, et al., 1997, *Science* 277, 1811–1815), and biochemically-tightly regulated (Thompson, 1992, *The Regulation of Membrane Lipid Metabolism.* CRC Press, Ann Arbor, pp 230), the sterol pathway has the potential to provide us chemotherapeutic targets not duplicated in humans (drug development).

Leishmania share with plants (and animals) that they rely on mevalonic acid as a precursor for de novo sterol synthesis (Holz, 1985, *Leishmaniasis.* Elsevier, N.Y., pp 79–92; Thimann, 1977, *Hormone Action in the Life of Plants.* University of Massachusets press, Amherst, pp. 448; Thompson, 1992, supra) However, the major sterol of leishmanial and fungal membranes, synthesized de novo by these parasites, is not cholesterol (like humans), but a 24-substituted sterol (ergosterol or episterol or provitamin D2). Ergosterol is synthesized by these parasites de novo from acetylCoA, to mevalonate, to squalene, to lanosterol, and 4 steps later to ergosterol (Holz, 1985, supra). Coppens and Courtoy (1995, *Mol Biochem Parasitol* 73, 179–188) showed that procyclics of *T. brucei* normally contain ergosterol synthesized de nova, a pathway shared with Leishmania.

However, Leishmania require cholesterol. Unlike man, but like closely related Kinetoplastid parasites, of the genus Trypanosoma, Leishmania "salvage" cholesterol from their environment, i.e., from macrophages and monocytes (the LDL/cholesterol plasma clearance cells) in the mammalian reticuloendothelial system. Free cholesterol and free fatty acids do not occur normally in plasma. The cholesterol esters of fatty acids, which are by themselves insoluble in plasma, are located in the low density lipoprotein, LDL, as a nonpolar core surrounded with a polar shell of phospholipids, apoprotein, and unesterified cholesterol, thus ensuring solubilization and transport (Ormerod & Venkatesan, 1982, *Microbiol Rev* 46, 296–307; Thompson, 1992, supra). Leishmania reside in mononuclear macrophages, which comprise the major part of low-density lipoprotein (LDL) plasma clearance system via both receptor and receptor-independent mechanisms (Goldstein & Brown, 1976, *Curr Top Cell Regul* 11, 147–181; 1977, *Ann Rev Biochem* 46, 897–930; Weisgraber, et al., 1978, *J Biol Chem* 253, 9053–9062; Pangburn, et al., 1981, *J Biol Chem* 256, 3340–3347; Bilheimer, et al, 1982, *Proc Natl Acad Sci USA* 79, 3305–3309; Haughan, et al., 1992, *Biochem Pharmacol* 44, 2199–2206). Transport of LDL-cholesterol via either or both mechanisms into infected monocytes would thus allow leishmanial parasites to meet their cholesterol requirement. Drugs which interrupt the quantity, transport, or delivery of cholesterol to the parasite would have potential to adversely affect leishmanial survival.

There are marked metabolic similarities between leishmanial and trypanosomal lipid acquisition and metabolism. Bloodstream forms of *Trypanosoma brucei* spp. can ingest particulate fat (Wooten & Halsey, 1957, Parasitol 47, 427–431), and, like Leishmania, *Trypanosoma brucei rhodesiense* depends on the cholesterol of their habitat (Dixon et al., 1972, *Comp Biochem Physiol* 41B, 1–18).

Coppens and colleagues (1995, *Mol Biochem Parasitol* 73, 179–188) showed that the enzyme inhibitor, synvinolin (simvastatin or Zocor®), potentiates growth inhibition of *Trypanosoma brucei* in the presence of drugs interfering with the exogenous supply of cholesterol; and conversely, growth inhibition by synvinolin can be reversed by LDL, mevalonate, squalene or cholesterol. Coppens and Courtoy (1995, supra) showed that procyclics of *T. brucei* spp. normally incorporate exogenous cholesterol in their membranes. These investigators further demonstrated that growth of the culture-adapted trypanosomes is accelerated by supplementation of the medium with low density lipoprotein (LDL) particles which were endocytosed by the parasites via a receptor-mediated mechanism.

We observed that traditional medical herbal therapies, containing plant sterols having the cholestane backbone but with hydrophillic substitutent side chains, first destabilized then killed parasites in vitro in a dose-dependent manner. Chemical analyses of the structure of the antiparasitic active moieties from these plants (>70 tested) most frequently revealed an isoprenoid, terpenoid, or steroidal structure resembling but not duplicating normal mammalian sterolgenic precursors. It is known, as previously discussed, that Leishmania spp. and African Trypanosoma spp. take up cholesterol and any cholestane-backbone molecule (Dixon, et al., 1972, supra; Haughan, et al. 1995, supra). We believe that substitute "plant cholesterol-like" molecules serve to destabilize parasites' membranes because of either addition of new hydrophillic sidegroups; or replacement of typically hydrophobic side-groups with more hydrophillic sidegroups. These observations, in addition to the knowledge of the importance of cholesterol and cholesterol synthesis in the organism, appeared to validate the use of these medicinal plants as herbal remedies for treatment of protozoan parasitic infections.

Therefore, at several points within the sterol synthesis and cholesterol salvage pathways, we have identified molecules chemically or functionally similar to the natural component, but which act to shut-down leishmanial function.

Therefore, it is one object of the present invention to provide a novel method for identifying compounds having antiparasitic and antifungal activity based on the physiological action of the compounds in the sterol synthesis and/or metabolism, and/or excretion pathway of the parasite.

It is also an object of the present invention to provide a novel method for identifying antifungal and antiparasitic compounds by their ability to inhibit cholesterol synthesis and/or metabolism and/or excretion, directly or indirectly.

It is further an object of the present invention to provide novel antiparasitic and antifungal agents which are capable of oral administration, and are efficacious and less toxic alternatives to agents heretofore used for the treatment of fungal and/or parasitic infection in humans and animals.

A still further object of the present invention is to provide a novel method of using existing compounds not previously known to have antifungal or antiparasitic activity for the prevention and/or treatment of fungal or parasitic infection in humans and animals.

It is also an object of the present invention to provide antiparasitic and antifungal compositions for either prophylactic or field treatment.

A further object of the present invention includes the combined therapy that can be obtained by treating patients with leishmania, trichomoniasis, or trypanosomiasis, with a combination of the compounds of the present invention, preferbly the combination is chosen such that compounds which inhibit different parts of the cholesterol pathway are combined.

BRIEF DESCRIPTION OF THE DRAWINGS

These and other features, aspects, and advantages of the present invention will become better understood with reference to the following description and appended claims, and accompanying drawings where:

DETAILED DESCRIPTION

Figure 1:
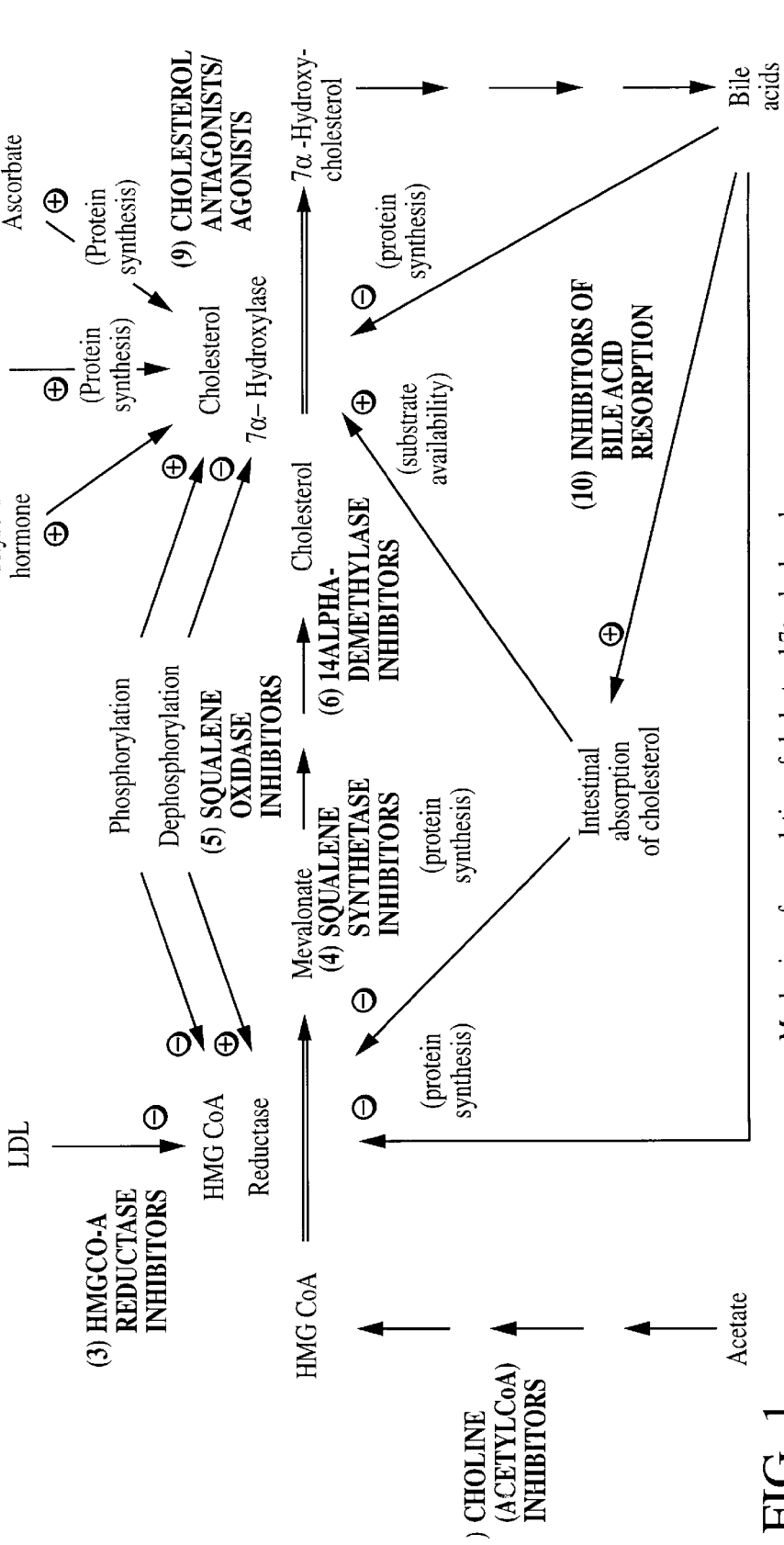
FIG. 1. A schematic representation of the mechanism of cholesterol regulation indicating eleven types of inhibitors of lipid metabolism, synthesis, or excretion having antiparasitic/antifungal properties (bold cap letters).

Forty-two medicinal plants were identified as having antileishmanial properties from ethnomedical studies and either antileishmanial/antifungal properties from ethnobotanical research. Fifty percent (21/42) plants and 59/121 extracts tested showed in vitro antileishmanial activity. The chemical isolation strategy focused preferentially on isolation of di- and tri-terpenes (sterol-like) compounds which seemed to contain highly active (>90% cidal in vitro) antileishmanial compounds. The first compound to be characterized was a spirostanol saponin, Mannispirotan A, isolated from the fruit pulp of Dracaena manii (Okunji et al., 1990, Int J Crude Drug Res 28, 193–199). Study of the structure (shown below at 'A') revealed a resemblance to a sterol nuclei structure.

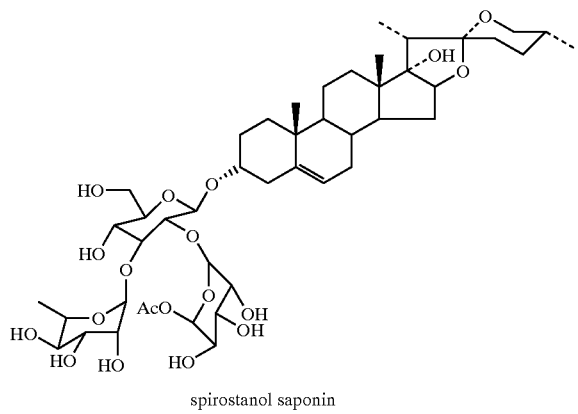

spirostanol saponin

Four additional highly active extracts have been purified and their structures, which include more than 25 separate compounds, determined. Most are compounds that have chemical congeners, isoprenoids, di- and triterpenoids common to lipid metabolism; a few are berberine-like or -dimers presented in U.S. Pat. No. 5,290,553, to Iwu, et al., 1994. All documents cited herein supra or infra are incorporated in their entirety by reference thereto. Knowledge of structure activity relationship (SAR) has allowed us to formulate hypotheses for the mechanism of antiparasite physiologic inhibition.

When additional plant extracts were examined, and additional active structures elucidated, namely, Sakuretin from Eupatorium odoratum, Labdane-dial from Aframomum danielli, and Afromomum aulocacarpus, unexpectedly, the structures of these compounds did not resemble cholesterol, but instead resembled Vitamin D2 and possible parts of a squalene isoprenoid structure as it is cyclized.

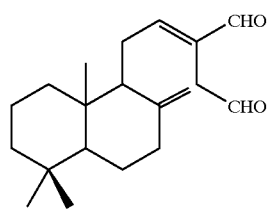

Labdane-dial from Aframomum danielli

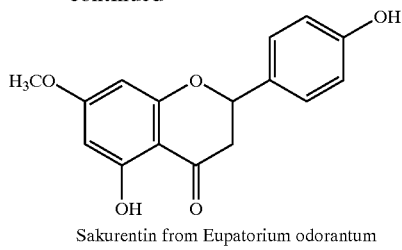

Sakurentin from Eupatorium odorantum

As discussed previously, the parasite can synthesize ergosterol (Holz, 1985, supra), also known as pro-vitamin D2 (structure shown below) but they require cholesterol which cannot be synthesized by the organism, and therefore, has to be salvaged from the host. When leishmania infects a host, within minutes, the organism localizes to the liver, and it is in the liver that host ergosterol (provitamin D) is converted to vitamin $D_2$. The conversion of ergosterol to cholesterol causes an increase in $Ca^{++}$ ion concentration. It had been reported previously that the ability of macrophages to kill leishmania is reduced under increased $Ca^{++}$ conditions (Olivier, 1996, Parasitol-Today 12, 145–150).

The structures of the active ingredients in the medicinal plants, and the fact that the parasites must have to scavenge cholesterol, made us focus on the cholesterol synthesis pathway as described in FIG. 1.

We have found that drugs known to inhibit different parts of the cholesterol pathway can be, for the first time, used as antiparasitic agents. This discovery was novel and unexpected and was the result of putting together several different disparate pieces of evidence. None of the drugs discussed in this application were used or suggested for the treatment of leishmania, trypanosomiasis, or trichomoniasis. It is only after the elucidation of the chemical structure of the active compounds in the medicinal plants in addition to inventive activity that the relationship between the sterol pathway and possible antiparasitic agents was discovered. Most are human-use, FDA- approved drugs for alternative medical indications.

Our initial work focused on the following metabolic steps of leishmanial steroid metabolism which we have ascertained are critical for parasite survival: (1) butyric acid as a required precursor for both fatty acid and sterol synthesis; (2) mevalonic acid synthesis from acetylCoA; (3) squalene synthesis from mevalonic acid; (4) ergosterol synthesis from lanosterol; and (5) sterol (cholestane-analog uptake).

At each step and in each category of inhibitory compounds, suitable examples of drugs which may be used as antiparasitic/antifungal agents are mentioned. However, these examples are not meant to be limiting, and it is understood that other suitable drugs, known or to be discovered, which belong in the categories mentioned can be assayed and used as antiparasitic/antifungal agents. The assays for testing whether or not a drug is antiparasitic/antifungal are known, one of which is described in the Examples below.

Butyrate Inhibition

Butyrate is a key fatty acid precursor of acetyl-CoA. Acetyl-CoA and free fatty acids are critical to eukaryotic cells' energy production via beta-oxidation. Fatty acids are activated to acetyl-CoA derivatives, transported into the matrix of the mitochondria via the carnitine cycle, where they undergo beta-oxidation (Murray et al., 1988, Harper's Biochemistry, 21st ed., Appleton and Lange, Publ., Norwalk, Conn.). Beta-oxidation of fatty acids results in the reduced coenzymes FADH2 and NADH. The oxidation of 1 mole of FADH2 yields 2 moles ATP, and the oxidation of 1 mole of NADH yields 3 moles of ATP. From work in our laboratory, we know that butyrate is a key factor for leishmanial metabolism. Using $^{14}C$-labelled butyrate, we showed that it is readily taken up and rapidly metabolized to $^{14}CO_2$ by Leishmania spp. (Jackson, et al., 1989, Am J Trop Med Hyg 41, 318–330; Jackson, et al., 1990, Am J Trop Med Hyg 43, 464–480). Any compound comprising a butyrate inhibitor can be used as an antiparasitic/antifungal agent. Suitable forms of such compounds are cefaloglycin and xenbucine. Cefaloglycin reduces oxidation and uptake of butyrate. Cefaloglycin, 7-(2-amino-2-phenylacetamido)-3-(hydroxymethyl)-8-oxo-5-Thia-1-azabicyclo [4.2.0] acetate (ester), chemical registration no. 3577-01-3, or aminophenylacetamido cephalosporanic acids, are known in the art and marketed under the name Kafocin® by Eli Lilly and Co. Indianapolis, Ind. A process for their production is described in U.S. Pat. No. 3,422,103 to Wilfred et al., Jan. 14, 1969, herein incorporated in its entirety. Xenbucin, 2-(4-biphenyl) butyric acid; alpha-ethyl-[1,1'-biphenyl]-4-acetic acid, chemical ID no. 959-10-4, described in Brit. Patent 1,168, 542 (1969, Maggioni), preparation described in U.S. application Ser. No. 4,542,233 to Piccolo et al., September, 1985, marketed under the name Liosol® by Maggioni Pharmaceutici, Italy.

CHOLINE: Choline is the starting material for lipogenesis via production of acetyl-CoA. Dapsone (4,4'-diaminodiphenyl sulfone) has been reported active against human leishmaniasis via choline inhibition (Dogra, 1992, Infection 20, 189–191). This drug is believed to act via paraminobenzoic (PABA) acid-reversible block of the folic acid metabolism of parasitic protozoa. It is unlikely that this is the mechanism by which dapsone functions against Leishmania.

Leishmania rely exclusively on salvage mechanisms for purine synthesis and metabolism. Presumably, a dapsone block of purine synthesis via prevention of the reduction of folic acid to the tetrahydro-derivative and, thus, transport of the formyl carbon into the purine ring (positions 2 & 8 of purine), could not occur in leishmanial parasites utilizing preformed purines to synthesize nucleic acids and lacking these de novo synthetic pathways. Likewise, a thymidylate synthetase block is unlikely to prove fatal, since Leishmania salvage as well as synthesize pyrimidines.

A choline inhibitory pathway for antileishmanial activity (as suggested by Dogra, 1991, Trans R Soc Trop Med Hyg 85, 212–213; Dogra, 1992, supra) is more likely, although the mechanism of such inhibition, is a more complex problem to investigate. Dogra (1991, supra;1992, supra) postulated that dapsone probably acts against Leishmania by inhibition of choline incorporation into lecithin in the cell membrane, thus decreasing phospholipid synthesis. It is the relationship of choline inhibition to other drug-sensitive lipid metabolic target(s) that we wish to investigate therapeutically.

Dapsone has an $IC_{50}$ of 600 mM (1.49 mg/ml) in vitro against Leishmania major promastigotes in a chemically defined medium. Dapsone inhibition was not reversible by p-aminobenzoate (PABA) folate or thymidine (Peixoto and Beverley, 1987, Antimicrob Agents Chemother 31, 1571–1578). Invanetich and Santi (1990a, FASEB J 4, 1591–1597) noted that: "Anti-folates commonly used to treat microbial infections are poor inhibitors of Leishmania major dihydrofolate reductase." Peixoto and Beverley (1987, supra) concluded that "the mode of action of sulfa drugs [dapsone] is not by the classical route of de novo folate synthesis". These results with dapsone inhibition are understandable based on previous work on the folate metabolism of these protozoan parasites.

Clofazimine, N,5-Bis(4-chlorophenyl)-3,5-dihydro-3-[(methylethyl)imino]-2-phenazinamine; 3-(p-choroanilino)-10-(p-chlorophenyl)-2,10-dihydro-2-(isopropylimino) phenazine, chemical registration no. 2030–63–9, marketed as Lamprene®, an anticancer and antimycobacterial riminophenazine drug, is active via phospholipase A2-mediated oxidative and nonoxidative mechanisms (Arunthathi and Satheesh 1997, *Lepr Rev* 68(3), 233, 241; Ruff et al., 1998, *Ann Oncol* 9, 217–219; Van Rensburg, et al., 1993, *Cancer Res* 53, 318–323; Venkastesan, et al., 1997, *Lepr Rev* 68, 242–246). Antimycobacterial dose is 50 mg/day or 100 mg on alternate days (Venkastesan, et al., 1997, supra). Riminophenazine drugs have never been used or proposed as antileishmanial/antitrypanosomals. Human dose recommended are 100–200 mg/day, although doses 400 mg–600 mg/day can be given.

Other suitable examples of inhibitory compounds include eldacimibe, 1,3-Dioxane-4,6-dione,5-[[[3,5-bis(1,1-dimethylethyl)-4-hydroxyphenyl]amino][[[4-(2,2-dimethylprophyl)phenyl]-methyl]hexylamino]methylene]-2,2-dimethyl-;(2) Cyclic isopropylidene[(3,5-di-tert-butyl-4-hydroxyanilino)[hexyl(p-neopentyl-benzyl)amino]methylene]malonate, chemical registration no. 141993-70-6, marketed as Eldacimibe® by Wyeth-Ayerst Laboratories, Philadelphia, Pa., and lecimibide, Urea, N'-(2,4-difluorophenyl)-N-(5-((4,5-diphenyl-1H-imidazol-2-yl)thio-)pentyl)-N-heptyl-, chemical registration no. 130804-35-2, marketed as Lecimibide® by Merch Pharmaceutical Co., Whitehouse Station, N.J.

Squalene

Some compounds act indirectly on the Leishmania as steroidal synthesis regulators: human insulin, human transferrin, and low density lipoprotein (LDL). Both transferrin and insulin are either inhibitors or growth stimulants of human and, possibly also, leishmanial sterol synthesis depending on concentration (Schroepfer, 1981, *Ann Rev Biochem* 50, 585–621; Thompson, 1992, *The Regulation of Membrane Lipid Metabolism.* CRC Press Ann Arbor, pp 230; Jackson, et al., 1989, supra). Other sterols, synthesized only by the Leishmania and fungi, may act to regulate the host cells (monocyte or macrophage) to prevent parasite killing, e.g. by increasing intracellular $Ca^{++}$ level (Oliver, 1996, supra). Sacchettini and Poulter (1997, *Science* 277, 1788–1789) noted that the isoprenoids, or steroidal building blocks, are a remarkably diverse chemical class comprising over 23,000 individual compounds. For over 100 years, dating back to traditional medicine, it has been known many antifungals also sometimes have antiparasitic properties (reviewed, Steck, 1972, *The Chemotherapy of Protozoan Diseases,* Vol II, p 7.61–7.63 and 11.100–110, U.S. Government Printing Office, Washington, D.C., #O-462-576). Additionally, it has been known for over 50 years that antifungals such as amphotericin B, pentamidine, and ketoconazole (Neal, 1987, *The Leishmaniases in Biology and Medicine, Vol II Clinical Aspects and Control.* Academic Press, New York, pp. 793–845) have antileishmanial activity. Lipid analyses of several Leishmania spp. revealed that these parasites' membranes contain a high percentage of ergosterol, a sterol most frequently found in fungi and some bacteria (Holz, 1985, supra) which presents a basis for common mechanism of action of antifungal drugs on leishmania. Terbinafine is recognized as an clinical antifungal and cutaneous antibacterial (Back, et al., 1992, *Brit J Dermatol* 126 (Suppl 39), 14–18; Baudraz-Rosselet et al., 1992, *Brit J Dermatol* 126 (Suppl 39), 40–46; Finlay, 1992, *Brit J Dermatol* 126 (Suppl 39), 28–32; Goodfield, 1992, *Brit J Dermatol* 126 (Suppl 39), 33–35; Hay and Stratigos, 1992, *Brit J Dermatol* 126 (Suppl 39), 1–69; Haroon, et al., 1992, *Brit J Dermatol* 126 (Suppl 39), 47–50; Hull and Vismer, 1992, *Brit J Dermatol* 126 (Suppl 39), 51–55; Kovarik, et al., 1992, *Brit J Dermatol* 126 (Suppl 39), 8–13; Nolting and Brautigam, 1992, *Brit J Dermatol* 126 (Suppl 39), 56–60; Roberts, 1992, *Brit J Dermatol* 126 (Suppl 39), 23–27; Ryder, 1992, *Biochem J* 230, 765–770; Van der Schroeff, et al., 1992, *Brit J Dermatol* 126 (Suppl 39), 36–39; Villars and Jones, 1992, *Brit J Dermatol* 126 (Suppl 39), 61–69).

Recent antiparasite investigations of known antifungals have primarily involved the combination of known antileishmanials with one or more newer antifungals, the latter to include the squalene oxidase inhibitor, terbinafine. The antifungal terbinafine has shown preliminary antitrypanosomal activity in vitro and in primary rodent drug screening systems against Trypansoma cruzi, the etiologic agent of Chagas' disease (Urbina et al., 1996, *Science* 273, 969–971) and Leishmania mexicana, 2 cutaneous leishmanial subspecies (Goad et al., 1985, *Biochem Pharmacol* 34, 3785–3788; Berman and Gallalee, 1987, *J Parasitol* 73, 671–673).

Complex structure activity relationship (SAR) studies of synthetic and natural product (biologically derived) squalene synthetase and squalene oxidase inhibitors have shown several such compounds have in vitro and in vivo activities having human hypocholesteremic potential. Abe and collegues (1994, supra) reviewed SAR data from 284 squalene synthesis inhibitors. Selected data from a few of the best hypocholesteric candidates (from Abe, et al, 1994 supra) follow.

Suitable examples of Squalene Synthetase inhibitors include:

1. Thioether analog of 2,3-oxidosqualene (Abe, et al, 1994, supra; Zheng, et al, 1995, *J Am Chem Soc* 117, 670–680 ) $ICC_{50}$ 0.0023 uM
2. 29-methylidene-2,3-oxidosqualene, an irreversible inhibitor of oxidosqualene cyclase (Abe, et al, 1994, supra; Xiao and Prestwich, 1991, *J Am Chem Soc* 113, 9673–9674)
3. Ether analog of farnesyl diphosphate ($IC_{50}$ 0.05 uM, Abe, et al, 1994, supra)
4. Farnesyl bisphosphonate (no oral activity, $IC_{50}$ 0.00027 uM, Abe, et al, 1994, supra)
5. Natural product from Phoma sp. C2932, Squalestatins 1,2,3 ($IC_{50}$ 15.2, 15.1, 5.9 nM, respectively, Abe, et al, 1994, supra)
6. Natural products from ATCC 20986, *Sporormilla intermedia,* and *Leptodontium elatius:* Zaragozic acid A,B,C, $IC_{50}$ 78, 29, 45 pM , respectively (Abe, et al, 1994, supra)
7. CP-225,917 (Pfizer) and CP-263,114 (Pfizer), both compounds inhibit squalene synthase and farnesylprotein transferase (Borman, 1999, *Chemical and Engineeing News* Jun. 7, 1999, 8–9; Service, 1999, Science 284, 1598–1599; Dabrah et al., 1997, *J Antibiot* 50, 1–7)

Suitable examples of inhibitors of Squalene Oxidase include:

1. Naftifine, 1-Naphthalenemethanamine, N-methyl-N-(3-phenyl-2-propenyl)-(E), chemical registration no. 65472-88-0, marketed as an antifungal under Exoderil® or Naftin®, and described in a patent to Berney on Aug. 4, 1981, U.S. Pat. No. 4,282,251. IC$_{50}$ 0.93 uM (Abe et al, 1994, supra; Georgopoulis et al., 1981, *Antimicrob Agents Chemother* 19, 386–389; Paltauf et al., 1982, *Biochim Biophys Acta* 712, 268–273; Petranyi et al., 1984, Science 224, 1239–1241; Ryder, 1984, In Nombel C. (ed.) *Microbial Cell Wall Synthesis and Autolysis,* Elsevier, N.Y., pp 313–321)

2.Terbinafine, 1-Naphthalenemethanamine, N-(6,6-dimethyl-2-hepten-4-ynyl)-N-methyl-, (E)-, an antimycotic allylamine, chemical registration no. 91161-71-6, or turbinefine hydrochloride, chemical registration no. 78628-80-5. Turbinafine is marketed as Lamisil®, and its preparation is described in Eur Patent Appl. no. 24,587 to A. Stutz, 1981. Terbinafine has been shown to have activity against Leishmania species in vitro and in animal and human clinical trials (Abe, et al, 1994, supra; Bahamdan et al., 1997, *Int J Dermatol* 36, 59–60; Ellenberger and Beverley, 1989, *J Biol Chem* 264, 15094–15103; Goad, et al., 1985, Biochem Pharmacol 34, 3785–3788; Gonzales-Ruperez et al., 1997, *Dermatology* 194, 85–86; Rangel et al., 1996, *Antimicrob Agents Chemother* 40, 2785–2791; Urbina 1997, Parasitology 114 Suppl S91–S99; Vannier-Santos et al., 1995, *J Eukaryot Microbiol* 42, 337–346).

3. Butenafine, N-(p-tert-Butylbenzyl)-N-methyl-1-naphthalenemethylamine, a benzyl amine antifungal, chemical registration no. 101828–21–1, or butenafine hydrochloride, chemical registration no. 101827-46-7, marketed as Mentax® by Penederm Inc. Foster City, Calif. Preparation is described in U.S. Pat. No. 4,822,822 to Arita et al. on Apr. 18, 1989.

4.SDZ 87–469 (Georgopapadakou et al., 1992, *Antimicrob Agents Chemother* 36, 1779–1781, and references cited therein; Ryder and Frank, 19992,*J Med Vet Mycol* 30, 452–460) IC$_{50}$ 0.011 uM (Abe, et al, 1994, supra)

5.NB-598, (Matzno et al., 1997, *J lipid Res* 38, 1639–1648 and references cited therein) IC$_{50}$ 0.75 nM (Abe, et al, 1994, supra)

6. TMD, 4,4,10beta-trimethyl-trans-decal-3beta-ol (Abe, et al, 1994, supra; Nelson et al, 1978, *J Am Chem Soc* 100, 4900–4902)

HMGCoA, 3-hydroxy-3-methylglutaryl CoA Reductase Inhibitors

Mevalonic acid, a precursor to human sterols and steroids; and in plants, to hormones and carotenoids, is available to Leishmania both via the host human monocyte or macrophage; and within the sandfly vector, in the bloodmeal and plant juices essential to sustain the fly (Leclercq, 1969, *Entomological Parasitology.* Pergamon Press, New York, pp 158; Beytia and Porter, 1976, *Ann Rev Biochem* 45, 112–142; Thimann, 1977, *Hormone Action in the Life of Plants.* University of Massachusetts Press, Amherst, pp 448; Caspi, 1984, Tetrahedron 42, 3–50). Most sandfly species known to transmit Leishmania, require not only blood but also plant fluids to maintain proper hydration for survival. Avoiding lethal ultraviolet rays of sunlight, sandflies rest in moist shady areas during the day to emerge in the evening to feed. Plants, particularly those in the tropical climates where sandflies are most numerous, tend to lose water in the intense heat of the afternoon. The plant hormone responsible for closing leaf stomata to prevent plant dehydration, abscisic acid, is made in response to water loss. Abscisic acid is known to increase 200-fold in a dehydrated plant. Three mevalonic acid molecules are required to produce one molecule of abcissic acid. As more abscisic acid is required in the heat of the day, so is its precursor, mevalonic acid. Sandflies feed at twilight when plant dehydration, abscisic acid, and melvalonic acid would be expected to be near peak daily level in tropical plants.

In animals and humans, mevalonic acid is also an important precursor to sterol and steroid synthesis, so would likewise be available to leishmanial amastigotes inhabiting the monocytes, macrophages and hepatic cells. On the basis of host and vector physiology alone, mevalonic acid appeared to be implicated as an important precursor molecule for leishmanial sterolgenesis.

To investigate this, we used $^{14}$C-mevalonic acid to determine rate of incorporation by Leishmania (1.0 ng/hr/108 parasites at 25° C, using the respirometric assay. We also looked at mevalonic acid catabolism and found mevalonate is sparingly metabolized to $CO_2$ (less than 1/25 the rate of aspartic acid metabolism, a most rapidly catabolized amino acid, Jackson, et al., 1989,*Am J Trop Med Hyg* 41, 318–330) even when the promastigotes are maintained under starvation condition for 30 minutes. When mevalonate was added as a nutritional supplement the parasites grew profusely but less rapidly than parallel unsupplemented control cultures. (The amount mevalonate added to in vitro cultures was determined based on incorporation rate relative to aspartic acid, and this may have resulted in too high an estimated mevalonic acid concentration.) However, mevalonate-fed cultures remained in logarithmic phase growth 2-fold longer (>10 days) than parallel unsupplemented cultures (which ended log phase growth at 4–5 days of culture). Given these preliminary observations: it appears Leishmania (a) incorporate mevalonic acid readily from their environment; (b) catabolism is spared even under starvation conditions; and (c) mevalonic acid can act as a nutritional supplement in vitro.

Three-hydroxy-3-methylglutaryl CoA reductase is a protein of the endoplasmic reticulum whose concentration is determined by rates of cholesterol synthesis. HMG-CoA reductase catalyzes the reductive deacylation of HMG-CoA to mevalonate by two molecules of NADPH. In most tissues this is considered the first committed step in sterol/isoprenoid biosynthesis. In most biologic systems studied, this reaction is the rate-limiting step for sterol biosynthesis (Danielsson and Sjovall, 1985). Most widely used hypercholesteremic drugs have their mode of action at this irreversible synthetic step catalyzed by 3-hydroxy-3-methylglutaryl CoA reductase (HMCoAR).

HMG-CoA reductase inhibitors lower plasma total cholesterol, low density lipoprotein (LDL), and B apolipoprotein in humans as the result of decreased cholesterol synthesis and enhanced removal of LDLs via the LDL receptor pathway in hepatocytes (Hoeg and Brewer, 1987; Tolbert, 1987).

No HMG-CoA reductase inhibitor has ever been used or previously tested as an antileishmanial or for South and Central American *Trypansoma rangeli.* There are two references to anti-Trypanosoma (Schizotrypanum) *cruzi,* South and Central American trypanosome species, in vitro (Florin-Christensen, et al., 1990; Urbina, et al., 1993) and in vivo mouse testing of mevinolin (Lovastatin®) testing, alone and in combination with ketoconazole and terbinafine (Urbina, et al., 1993). Coppens and colleagues (1995; and, Coppens and Courtoy, 1995) showed that the enzyme inhibitor, synvinolin (simvastatin or Zocor®), potentiates growth inhibition of *Trypanosoma brucei* in the presence of drugs interfering with the exogenous supply of cholesterol; and conversely, growth inhibition by synvinolin can be reversed by LDL, mevalonate, squalene or cholesterol.

All 3-hydroxy-3-methylglutaryl CoA reductase inhibitors, or vastatins, are not a chemical class effect but vary widely between HMGCoA reductase inhibitors (Bocan, et al., 1994; Haruyama, et al., 1986; Kempen, et al., 1991; Nakaya, et al., 1986; Serizawa, et al., 1983; Tsujita, et al., 1986; Yoshino, et al., 1986)(e.g. atorvastatin, CI981; PD134965; pravastatin, CS-514, Eptastatin, SQ 31000; BMY22089; simvastatin, Synvinolin, MK-733; monacolin K, MB-530B; mevinolin, lovastatin; mevastatin, ML-236B, Compactin) do not have the same efficacy for preventing atherosclerotic lesions, inhibition of cholesterol synthesis in target tissue(s), reducing cellular accumulation of free and/or esterified cholesterol, degradation of LDL, or synthesis of phosphotidylcholine and sphingomyelin.

This observation may be due, in part to the chemical design of various vastatins, for example, pravastatin differs from other HMG-CoA reductase inhibitors in two aspects. In pravastatin, the 6-position on the decalin ring is occupied by a hydroxyl group, whereas, in lovastatin and simvastatin, this same position is occupied by a methyl group. This difference in structure is responsible for the different physiochemical properties of these drugs and confers on pravastatin its hydrophilic characteristics. Lovastatin and simvastatin are hydrophobic and designed with the objective of obtaining high levels of hepatoselectivity (Keidar, et al., 1994; Sirtori, 1993). Pravastatin is administered as a sodium salt of an open acid and is the active inhibitor of HMG-CoA reductase; lovastatin and simvastatin are prodrugs and are given as inactive lactones that, following oral administration, are hydrolyzed to an active inhibitor" (Keidar, et al., 1994). Pravastatin is manufactured by Bristol-Myers Squibb; Merck manufacturers lovastatin and simvastatin (Zurer, 1997); and Sanyo, eptastatin (Yoshino, et al., 1986).

Suitable HMG-CoA reductase inhibitors include:

1)Pravastatin, [1S-(1-alpha(beta-S*,delta-S*),2-alpha, 6-alpha,8-beta(R*),8a-alpha]]-1,2,6,7,8,8a-hexahydro-2-methyl-8-(2-methyl-1-oxobutoxy)-beta,delta,6-trihydroxy-1-Naphthaleneheptanoic acid monosodium salt, a highly selective cholesterol synthesis inhibitor of hepatic, intestinal cells (ileum), and in monocyte-derived macrophages (Keidar, et al., 1994). Pravastatin, chemical registration no. 81093-37-0, marketed as Pravachol® by Bristol-Myers Squib, Wallingford, Conn. or as Eptastatin from Sanyo, as well as others. The preparation of pravastatin is described in U.S. Pat. No. 4,346,227 to Terahara et al., August, 1982. When humans were given a dose of 40 mg/day for 8 weeks, pravastatin resulted in a dose-dependent inhibition of macrophage cholesterol synthesis; LDL increased 119% with 0.1 mg/ml pravastatin; <or =0.19 mg/ml increased cholesterol esterification; >0.19 mg/ml inhibited cholesterol esterification; pravastatin inhibited cholesterol synthesis 55–62% and increased LDL degradation by 57% (Keidar, et al., 1994).

2)Simvastatin, [1S-[1-alpha(beta-S*,delta-S*), 2-alpha, 6-alpha,8-beta(R*),8a-alpha]]2,2-dimethylbutanoic acid 1,2,3,7,8,8a-hexahydro-3,7-dimethyl-8-[2-(tetrahydro-4-hydroxy-6-oxo-2H-pyran-2-yl)ethyl]-1-naphthalenyl ester, a competitive inhibitor of HMG-CoA reductase, chemical registration no. 79902-63-9, marketed in several forms, e.g. Zocor® from Merck & Co., Whitehouse Station, N.J., preparation described in U.S. Pat. No. 4,444784 to Hoffman et al. April, 1984. In a longterm study of simvastatin (3–5.4 years) at doses 0.5 of pravastatin and 0.125 of fluvastatin, simvastatin (at 10 to 40 mg/day doses) lowered serum cholesterol from baseline 20–40%; lowered low density lipoprotein cholesterol 35–45%; and reduced triglycerides 10–20% (Plosker G L, McTavish D, 1995).

3)Fluvastatin, 6-Heptenoic acid, 3,5-dihydro-7-[3-(4-fluorophenyl)-1-(1-methylethyl)-1H-indol-2-yl-]-[R*,S*-(E)]-, (+–)-, chemical registration nos. 93957-55-2 and 93957-54-1, marketed as Lescol® from Sandoz, East Hanover, N.J., described in U.S. Pat. No. 4,739,073, 1984. Review of Pharmacology and therapeutics use, Levy et al., 1993, Circulation 87, Suppl III-45 to III-53.

4)Atorvastatin, 1H-Pyrrole-1-heptanoic acid, 2-(4-fluorophenyl)-beta,delta-dihydroxy-5-(1-methylethyl)-3-pheny-1-4-[(phenylamino)carbonyl]-, [R-(R*,R*)]-, chemical registration nos. 134523-00-5 and 11086248-1, described in U.S. Pat. No. 5,273,995 to Roth, December 1993, marketed by Warner-Lambert, Morris Plains, N.J.

5)Cerivastatin, 7-[4-(4-fluorophenyl)-5-(methoxymethyl)-2,6-bis(1-methylethyl)-3-pyridinyl]-3,5-dihydroxy-, monosodium salt, [S-(R*,S*-(E))]]-, cerivastatin sodium, chemical registration no 143201-11-0, marketed as Baycol® from Bayer Corp. West Haven, Conn.

6)Crilvastatin, L-Proline, 5-oxo-, 3,3,5-trimethylcyclohexyl ester, chemical registration no. 120551-59-9, available from Laboratoire Pan Medica, France.

7)Dalvastatin, 2H-Pyran-2-one,tetrahydro-6-[2-(2-(4-fluoro-3-methylphenyl)-4,4,6,6-tetramethyl-1-cyclohexen-1-yl]ethenyl]-4-hydroxy-, [4R-(4-alpha,6-beta(E)]]-, chemical registration nos. 135910-20-2, 132100-551, available from Rhone-Poulenc Rore Pharmaceuticals, Inc. Collegeville, Pa.

8)Lovastatin, Butanoic acid, 2-methyl-,1,2,3,7,8,8a-hexahydro-3,7-dimethyl-8-[2-(tetrahydro-4-hydroxy-6-oxo-2H-pyran-2-yl)ethyl]-1-naphthalenyl ester,[1S[1alpha(R*), 3alpha,7beta,8beta(2S*,4S*), 8abeta]]-, chemical registration no. 75330-75-5, marketed in several forms, e.g. Mevacor® from Merck & Co., Inc. Whitehouse, N.J., described in U.S. Pat. No. 4,231,938 to Monaghan et al., November 1980, and G. S. Brenner et al., in *Analytical Profiles of Drug Stubstances and Excipients,* vol 21, H.g. Brittain, Ed. (Academic Press, San Diego, 1992) pp 277–305.

9)Mevastatin, Butanoic acid, 2-methyl-,1,2,3,7,8,8a-hexahydro-7-methyl-8-[2-(tetrahydro-4-hydroxy-6-oxo-2H-pyran-2-yl)ethyl]-1-naphthalenyl ester,[1S-[1-alpha(R*),7-beta,8-beta(2S*,4S*),8a-beta]]-, chemical registration no. 73573-88-3, marketed is several forms, e.g. Compactin® from from Merck & Co., Inc. Whitehouse, N.J., and described in U.S. Pat. No. 3,983,140 to Endo et al., September 1976 and reviewed in Endo, 1985, *J Med Chem* 28, 401–405.

Nonlipid Related Effects of Certain HMGCoA Reductase Inhibitors

Fluvastatin, simvastatin, and lovastatin (but not pravastatin) locally inhibit isoprenoid biosynthesis resulting in the following antiatherosclerotic effects on the arterial wall: a) inhibition of smooth muscle cell migration and proliferation (reversed by mevalonate); b) fluvastatin and simvastatin also inhibit cholesterol esterification and deposition induced by acetylated LDL in cultured macrophages (Corsini, et al., 1996). Simvastatin and lovastatin also reduce the rate of DNA synthesis and proliferation of a wide variety of cell types in vitro, by inducing a cell cycle arrest in G1 (Addeo, et al., 1996; Wilcken, et al., 1997). This effect of simvastatin and lovastatin on DNA synthesis arrest is antagonized by estrogen (Addeo, et al., 1996).

Inhibitors of Cholesterol Bile Acids Recycling: 7-alpha-hyroxylase and relationship to HMG-CoA reductase Cholesterol 7-alpha-hyroxylase and HMG-CoA reductase are located near each other on the endoplasmic reticulum. Newly synthesized cholesterol seems to be the preferred substrate for cholesterol 7-alpha-hyroxylase and its diurnal rise correlates with rise in enzyme synthesis. This enzyme is intricately linked with sterol synthesis and it's regulation (Danielsson and Sjovall, 1985). Therefore, it seemed logical to assume that certain inhibitors of cholesterol-bile acid recycling from the intestine may have cholesterol lowering effects that would also act to lower host tissue cholesterol available to parasites.

However, although bile acid binding drugs have not proven, to date, to be active used alone against parasites, these compounds may enhance HMG-CoA reductase inhibitor activity as demonstrated by Hoogerbrugge, et al., 1990; Kuroda, et al., 1992; McTavish and Sorkin, 1991; and, Wiklund, et al., 1993. This combination of an HMG-CoA reductase inhibitor plus a bile acid binding drug is likely be more potent for antiparasitic therapy than any single HMG-CoA reductase inhibitor alone because of known enhanced anticholesteremic properties of the two drug types when administered together over either drug type given alone.

Medical concern that hypocholesteremics based on HMG-CoA reductase inhibition may result in untoward effects on nontarget tissues due to longterm physiologic consequences of depletion of mevalonate-derived isoprenoids led to examination of cholesterol inhibition further down the synthetic path, at squalene synthesis.

Cytochrome P450 Enzyme Inhibitors:14ALPHA-Demethylase Inhibition and Delta 24(25) Sterol Methyltransferase Inhibitors The cytochrome P450 enzymes are a family of iron-containing hemoproteins. The P450 enzymes are generally divided based on structure and function. Those involved in steroidogenesis, the CYP11, CYP17, CYP19, CYP21, and CYP27 subfamilies; and in the metabolism of cholesterol and bile acids, the CYP7 and CYP51 subfamilies exhibit a high degree of regio- and stereospecificity (Coon, et al., 1992; Mason and Hutt, 1997; Nebert, et al., 1991). Coincidentally, in evolutionary terms, those cytochrome P450 enzymes involved in steroidogenesis are also the oldest mammalian P450's. Therefore, shared P450 steroidal enzymes are the most likely to be common to both humans and more primitive fungal or protozoan parasites infecting humans. Therefore, drugs known to specifically inhibit these P450 steroidal enzymes may also inhibit similar P450 enzymes of older, more primitive organisms.

Imidazole drugs, using ketoconazole as an example, may then have antifungal/antiparasitic action for two reasons: (1) Direct action on parasite P450 steroidogenic enzymes reduces parasite de novo sterol synthesis, particularly fungal and protozoal-specific ergosterol synthesis via 14alpha-demethylase inhibition of lanosterol conversion to ergosterol. (2) Also, indirectly because the human host intracellular or blood environment where the parasites must obtain cholesterol by "salvage" is likewise depleted of this second sterol required for leishmanial and trypanosomal survival.

Imidazoles can inhibit transformation of lanosterol to either Ergosterol or Cholesterol (14alpha-). Imidazoles are typically considered "antifungals" for use in treatment of both superficial and systemic fungal infections (Heel, et al., 1982, *Drugs* 23, 1–28). However, various other physiologic drug effects with rising doses have resulted in use of these compounds for nonfungal indications. Examples of imidazoles include: ketoconazole, clotrimazole, aminoglutethimide, and etomidate. Doses and pharmacokinetics for imidazoles have been reviewed by Heel et al., 1982, supra.

The antifungal compound, ketoconazole, is believed to inhibit cholesterol biosynthesis via inhibition of the microsomal P-450 enzyme 14alpha-demethylase. Additional known drug activities affecting steroidogenesis of imidazoles in general and ketoconazol in particular include: (1) at therapeutic doses (200–600 mg/day) ketoconazole blocks testosterone synthesis in men (Feldman, 1986; Pont, et al., 1982) and at high dose regimens caused substantial inhibition of testicular and adrenal steroidogenesis (Feldman, 1986); (2) ketoconazole blocks 11beta-hydrolase and cholesterol side-chain cleavage for the adrenal steroidogenic pathway (Feldman, 1986); (3) ketoconazole inhibits renal 25-hydroxyvitamin D-24-hydroxyase (Vitamin D, an intracellular $Ca^{++}$ regulator) (Feldman, 1986).

The actions of ketoconazole (as a representative imidazole) decreased human patient plasma cholesterol between 27% (at 1200 mg/day) to 15% (at 200 mg/day) from pretreatment baseline (Feldman, 1986). Ketoconazole and two other related 24(25) sterol methyltransferase inhibitors were shown by Urbina, et al. (1995) to elucidate that 24-alkyl sterols are essential growth factors for Trypanosoma cruzi and that the preferred substrate of the delta 24(25) sterol methyltransferase in this organism is zymosterol.

Miscellaneous Hypocholesteremics

1) BERBERINES: The exception to these lipid cogener natural antiparasitics are several natural and synthetic berberine/berbine analogs (U.S. Pat. No. 5,290,553, to Iwu, et al., 1994). Berberine extracted from *Coptis chinensis*, lowered serum cholesterol level of mice fed a high cholesterol diet (Chen and Xie, 1986) and is a known hypocholesteremic. These natural and synthetic berberine/berbine analogs have been found to have potent antimalarial, antitrypanosomal, and antileishmanial properties (U.S. Pat. No. 5,290,553, to Iwu, et al., 1994)

2) BETA-CAROTENE AND LYCOPENE are moderate hypocholesteremics. Fuhrman, et al. (1997, *Biochem Biophys Res Commun* 233, 658–662) reported a 14% decrease in plasma LDL cholesterol, in humans given a dose of 60 mg/day tomato lycopene for 3 months. In vitro, J-774 A.1 macrophages' cholesterol synthesis was inhibited 63% or 73% from acetate, but not from mevalonate, following treatement with 10 uM beta-carotene or lycopene, respectively (Fuhrman, et al., 1997, supra).

3) ANTICANCER COMPOUNDS: In some cases, anticancer agents act because sterol synthesis in proliferating cells is ususally controlled by sterols that are produced intracellularly and is, independent of extracellular cholesterol (Danielsson and Sjovall, 1985, *Sterols and Bile Acids*. Elsevier, N.Y.). A linkage has been shown between de novo cholesterol synthesis and is required for completion of the cell cycle (Bottomley, et al., 1980, *FEBS Lett* 119, 261–264). It would be expected that such anticancer agents (e.g. estrogen/testosterone agonists/antagonists) would have some antiparasitic properties either by virtue of lowering the cholesterol of the parasites' enviroment within the mammalian host (including man) or by direct inhibitory action on the sterol/cholesterol synthetic pathway of the parasites. It is well known (see above discussion) that while parasite and mammalian sterol metabolic pathways differ in some basic fundamental steps, these pathways for sterol production and incorporation share many common substrates, enzyme cofactors, and result in the same products. Thus, it is not unreasonable to assume that an anticancer compound having a known mode-of-action targeting a pathway common to both parasites and mammals (including man) would have fundamental and significant antiparasite properties.

One example is ketoconazole, which at moderate (200–600 mg/day) or high dose regimens inhibits both testicular and adrenal steroidogenesis (Feldman, 1986, *Endocrine Rev* 7, 409–420). Examples include: ketoconazole, clotrimazole, aminoglutethimide, and etomidate. At 400 mg/3X/day ketoconazole, prostate cancer subjects showed clinical improvement with few and minor side effects (Feldman, 1986, supra; Singh et al., 1995, *J Assoc Physicians India* 43, 319–320; Larbi et al 1995, *Am J Trop Med Hyg* 52, 166–168; Trachtenberg, 1984, *J Urol* 132, 61; Trachtenberg, and Pont, 1984, *Lancet* 2, 433).

An second suitable example is tamoxifen, (Z)-2-[4-(1,2-Diphenyl-1-butenyl)phenoxy]-N,N-dimethylethanamine, (chemical registration no. 54965-24-1 and 10540-29-1, preparation described in U.S. Pat. No. 4,536,516 to Harper et al., August 1985), best known as a nonsteroidal estrogen agonist for breast cancer adjuvant therapy (Bryant and Dere, 1998, *Proc Soc Exp Biol Med* 217, 45–52; Major et al., 1998, *Orv Hetil* 139, 121–124; Muller et al., 1998, *Cancer Res* 58, 263–267). Among tamoxifen's known consequences is that it results in lowering of sterol synthesis and cholesterol levels in many body tissues, including significant decreases in total serum and low density lipoprotein (LDL) cholesterol levels, increase in high density lipoprotein subclass 2 cholesterol, and increase in apolipoprotein A-I, a decrease in apolipoprotein B, and a reduction in serum concentration of lipoprotein (a) in humans (Chang et al., 1996, *Ann Oncol* 7, 671–675; Elisaf et al., 1996, *Anticancer Res* 16, 2725–2728; Morales et al., 1996, *Breast Cancer Res Treat* 40, 265–270; Wasan et al., 1997, *J Pharm Sci* 86, 876–879), and Wistar rats (Vinitha et al., 1997, *Mol Cell Biochem* 168, 13–19). These effects on cholesterol may be due to a direct inhibition of delta-8-isomerase (see Gylling et al., 1995, *J Clin Oncol* 13, 2900–2905). A known side-effect during high-dose therapy (similar to central nervous system toxicty of antiestrogens of the clomiphene type) is cognitive impairment in 32% of patients, and 17% of standard-dose patients, compared to 9% of control patients (van Dam et al., 1998, *J Natl Cancer Inst* 90, 210–218).

A third example is the estrogen antagonist, Raloxifene, Methanone, [6-hydroxy-2-(4-hydroxyphenyl)benzo[b]thien-3-yl][4-[2-(1-piperidinyl)ethoxy]phenyl]-, (chemical registration no. 84449-90-1) which inhibits both copper mediated LDL oxidation as well as the cellular modification of LDL by murine peritoneal macrophages. Raloxifene is a more potent inhibitor of LDL oxidation than 17-beta-estradiol and (in rats) lowered cholesterol levels below control values within 4 days after initiation of treatment (Bryant and Dere, 1998, supra; Frolik et al., 1996, *Bone* 18, 621–627; Zuckerman and Bryan, 1996, *Atherosclerosis* 126, 65–75). Another estrogen antagonist, exemestane, 6-methyleneandrosta-1,4-diene-3,17-dione, chemical registration no. 107868-30-4, an irreversible inhibitor of steroidal aromatase, reduces total and HDL cholesterol and total triglyceride.

A fourth example is the antiestrogen, clomiphene citrate (Clomid®, Prepn: Allen et al., U.S. Pat. No. 2,914,563 in 1959 to Merrell); droloxifene/droloxifene citrate (Klinge Pharma, Germany) and Zuclomiphene (=Transclomiphene, Marion Merrell Dow) which are also know to have hypocholesteremic properties via inhibition of cholesterol biosynthesis (Ke et al., 1997, *Bone* 20, 31–39; Ramsey and Fredericks, 1977, *Biochem Pharmacol* 26, 1161–1167). Droloxifene was reported to reduce total serum cholesterol 65–70% compared to controls in rats (Ke et al., 1995, *Bone* 17, 491–496). Similarly, toremifene (and tamoxifen) are reported to inhibit the conversion of delta-8-cholesterol to lathosterol so that total and LDL cholesterol levels are lowered by downregulation of cholesterol synthesis. Thus, inhibition of the delta-8-isomerase may be the major hypolipidemic effect of these agents (Gylling, et al., 1995, supra).

Many antiestrogens seem to work because estrogen is known to elevate plasma cholesterol concentration (Klimis-Tavantzis et al., 1983, *J Nutr* 113, 320–327). However, the disadvantage is that these also seem to lower cholesterol biosynthesis in the central nervous system and neurotoxic effects are known for many antiestrogens including the clomiphene and derivatives (Ramsey 1978, *Biochem Pharmacol* 27, 1637–1640).

Other possible antiparasitic/antifungal compounds include:

Thyroid hormone antagonists, suitable examples include dextrothyroxine, D-4-(4-Hydroxy-3,5-diiodophenoxy)-3,5-diiodobenzylalanine; O-(4-hydroxy-3,5-diiodophenyl)-3,5-diiodo-, or D-thyroxine, chemical registration no. 51-49-0, and dextrothyroxine sodium, chemical registration no. 7054-08-2 and 137-57-1, marketed as Choloxin® by Knoll Pharmaceutical Co. Mount Olive, N.J., U.S. Pat. No. 2,889,363 to Ginger on June 1959.

Antihyperlipoproteinemic agents which inhibit cholesterol reabsorption as bile acids. Suitable examples include cholestyramine resin, chemical registration no. 58391-37-0 or 11041-12-6 (Ast and Frishman, 1990, *J Clin Pharmacol* 30, 99–106), marketed in several forms, e.g. Questran® from Bristol-Myers Squib, Wallingford, Conn. In the same category is colestipol, chemical registration no. 50925-79-6 or colestipol hydrochloride, 1,2-Ethanediamine,N-(2-aminoethyl)-N'-[2-[(2-aminoethyl)amino]ethyl]-, polymer with (chloromethyl)oxirane, chemical registration no. 37296-80-3, preparation described in U.S. Pat. No. 3,803,237 to Lednicer et al., April 1974, reviewed in Heel et al., 1980, *Drugs* 19, 161–180, and marketed as Cholestid® from Pharmacia and Upjohn, Inc. Kalamazoo, Mich.

Antihyperlipoproteinemics, suitable examples include:
clofibrate, Propanoic acid, 2-(4-chlorophenoxy)-2-methyl-, ethyl ester, chemical registration no. 637-07-0, described in Hassan and Elazzouny, 1982, *Anal Profiles Drug Subs* 11, 197–224, marketed in several forms, e.g. Atromid-S® from Wyeth-Ayerst, Philadelphia, Pa.

Antihyperlipoproteinemics which inhibit synthesis of VLDL, possibly by inhibiting synthesis of ApoB-100), for example, Gemfibrozil, Pentanoic acid, 5-(2,5-dimethylphenoxy)-2,2-dimethyl-; Valeric acid, 2,2-dimethyl-5-(2,5-xylyloxy)-, chemical registration no. 25812-30-0, preparation described in U.S. Pat. No. 3,674,836 to Creger on July, 1972, marketed in several forms, e.g. Lopid® from Parke-Davis, Morris Plains, N.J.

Antihyperlipoproteinemics which inhibit synthesis of cholesterol and increase fecal excretion of bile acids, and may decrease plasma HDL levels, e.g. Probucol, Acetone, bis(3,5-di-tert-butyl-4-hydroxyphenyl)mercaptole; 4,4'-[(1-methylethylidene)bis(thio)]bis[2,6-bis(1,1-dimethylethyl)phenol], chemical registration no. 23288-49-5, preparation described in U.S. Pat. No. 3,576,883 to Neuworth, M. B. on Apr., 1971, and its use as a cholesterol-lowering agent in U.S. Pat. No. 3,862,332 to Barnhart et al., on January 1975, marketed in several forms, e.g. Lorelco®, by Hoechst Marion Roussel, Inc. Kansas City, Mo.

Antihyperlipoproteinemics which inhibit cholesterol lumenal absorption resulting in reduced serum LDL and serum cholesterol (Morehouse et al., 1999, *J Lipid Res* 40, 464–474. For example, Tiqueside, beta-D-Glucopyranoside, (3beta,5alpha,25R)-spirostan-3-yl 4-O-beta-D-glucopyranosyl- chemical registration no. 99759-19-0, and Pamaqueside Spirostan-1]-one,3-[(4-O-beta-D-glucopyranosyl-beta-D-glucopyranosyl)oxy]-, (3beta,5alpha,25R)-; (2) 11-Oxo-(25R)-5alpha-spirostan-3beta-yl 4-O-beta-D-glucopyranosyl-beta-D-glucopyranoside, chemical registration no. 150332-35-7, both available from Pfizer Laboratories, New York, N.Y.

Inhibitors of type II fatty acid synthesis such as cerulenin, 2,3-Epoxy-4-oxo-7,10-dodecadionamide. Antifungal antibiotic isolated from several species, including Acremonium (Cephalosporium), Acrocylindrum, and Helicoceras. It inhibits the biosynthesis of several lipids by interfering with enzyme function, chemical registration no. 17397-89-6, preparation described in Boeckman and Thomas, 1977, (*J Am Chem Soc* 99, 2805).

Antineoplastic agents, suitable examples including Ifosfamide, N,3-bis(2-chloroethyl)tetrahydro-2H-1,3,2-Oxazaphosphorin-2-amine, 2-oxide; 3-(2-chloroethyl)-2-[(2-chloroethyl)amino]tetrahydro-1,3,2-Oxazaphosphorine,2-oxide, chemical registration no. 3778-73-2, preparation described in U.S. Pat. No. 3732,340 to Arnold et al. in May, 1973, reviewed in Schoenike and Dana, 1990, *Clin Pharm* 179–191, marketed in several forms, e.g. Ifex® from Bristol-Meyers Oncology Division, Princeton, N.J.

Anticholelitholytic agents such as monoctanoin, Octanoic acid, monoester with glycerol, Octanoic acid, monoester with 1,2,3-propanetriol, chemical registration no. 26402-26-6, preparation and use described in U.S. Pat. No. 4,205,086 to Babayan, May, 1980, marketed as Monoctanin® from Ethitek Pharmaceuticals Co., Skokie, Ill.

The compounds of the invention can be assayed by any techiques known in the art in order to demonstrate their antiparasitic/antifungal activity. Such assays include those described below in the Materials and Methods. Those compounds which are demonstrated to have significant antiparasitic/antifungal activity can be therapeutically valuable for the treatment or prevention of leishmania, trichomoniasis, and trypanosomiasis.

Pharmaceutical compositions comprising the inhibitive compounds or the salts thereof are provided by the present invention. Administration of these compositions include, but are not limited to, oral, intradermal, transdermal, topical, mucosal, intravenous, subcutaneous, intramuscular, intraperitoneal, and intranasal routes. More than one administration to the patient may be necessary. The optimum amount of the antiparasitic/antifungal agent varies with the weight of the patient being treated, with some amount ranges presented in the patents describing these agents. A range includes dosages of 0.1 mg/Kg/day to 50 mg/Kg/day.

A further embodiment of this invention includes the combined therapy that can be obtained by treating patients with parasitic or fungal diseases with a combination of the compounds of this invention. The combination is preferably chosen such that the inhibitory activity of the combined compositions is different, i.e. the pathway is blocked at different points. The efficacy of combined treatment could be substantially better than one composition alone due to the ability to modulate different effects of the compounds and possibly reducing side-effects or toxicity. The administration of the compounds in the combination could be simultaneous or sequential or in different dose forms including combinations of oral dose forms with injectables to name just a few.

The invention can be better understood by referring to the following examples which are given for illustrative purposes only and are not meant to limit the invention.

The following MATERIALS AND METHODS were used in the examples that follow.

Trypanosome (a) IN VITRO drug screening method: 14 clinical isolates of *Trypanosoma brucei rhodesiense* (agent of East African Sleeping Sickness) many of which are refractory to standard trypanocides such as diamidines and melarsoprol (Bacchi et al., 1990, *Antimicrob Agents Chemother* 34, 1183–1188) are maintained as laboratory infections in rats and mice and as frozen stabilates of blood forms. Six of these isolates have been cultivated as blood forms in modified Iscove's medium (Hirumi & Hirumi, 1989, *J Parasitol* 75, 985–989). These cultivated blood forms are fully infective and serve as the initial screen for trypanocides based on a 24 well culture plate system and readings done on duplicate wells using a Coulter Counter (Bacchi and Yartlett, 1993, *Acta Tropica* 54, 225–236; Bacchi et al., 1996, *Antimicrob Agents Chemother* 4, 1448–1453). This screen has proven highly reproducible, needs minimal drug since the volume is limited (1 ml medium/well) and is complete after 48 h. It has proven to be highly predictive of in vivo activity (e.g., Brun et al., 1996, *Antimicrob Agents Chemother* 40, 1442–1447; Bacchi et al., 1996, supra).

Usually plant extracts are screened vs. four isolates, *T. b. brucei* Lab 110 EATRO (veterinary parasite, and 3 strains of *T. b. rhodesiense* (KETRI 243, KETRI 243 As10-3 and KETRI 269). The latter are human clinical isolates refractory to arsenicals and diamidines (KETRI 243 and 243 As10-3) or DFMO KETRI 269 (Bacchi et al., 1990, supra). Extracts giving IC50 values at or below 100 ug/ml will be considered for further testing, using a more purified extract.

Trypanosome IN VIVO drug screening method: Extracts having significant activity in vitro (IC50 <10 ug/ml) along with reasonable evidence of selectivity in mammalian toxicity tests will be studied in in vivo screens. Initially the standard *T. b. brucei* Lab 110 EATRO mouse model will be used. Agents proving active in this model will be tested in the *T. b. rhodesiense* KETRI 243 and 269 model infections. These screens have proven effective in identifying in vivo trypanocidal activities of DFMO and other polyamine analogs, nuceloside analogs, arylguanylhydrzones and other agents (e.g., Bacchi et al., 1980, Science 210, 332–334; 1987, *Antimicrob Agents Chemother* 31, 1406–1413; 1990, supra; 1992, *Antimicrob Agents Chemother* 35, 2736–2740; 1997, Antimicrob Agents Chemother 41, 2108–2112). Usually compounds are given by i.p. injection once daily for 3 days. Animals surviving >30 days beyond the deaths of untreated, infected controls with no evidence of blood parasites are considered cured. Other routes used include i.v., per os and Alza mini osmotic pumps which are implanted under the skin and release 1 ?l of drug solution per h for 3 or 7 days. Agents or extracts proving active in the above screens will be studied in a standard CNS model infection (Jennings et al., 1983, *Contrib Microbiol Immunol* 7, 147–154) which we have used to demonstrate efficacy of single agents or drug combinations (e.g., Clarkson et al., 1983, *Proc Natl Acad Sci* 80, 5729–5733; Bacchi et al., 1987, supra; 1996, supra), This model takes 10–12 months to resolve and will only be used for highly active extracts and purified substances.

Trichomonad In Vitro and in Vivo Drug Screening Methods.(a) In Vitro: Several strains of *T. vaginalis* are maintained, covering the spectrum of metronidazole resistance: CDC85 (highly resistant); RU384, RU383, IR78 (moderately resistant); NYH286, RU284, RU393, C1-NIH (sensitive). These strains are routinely cultivated in a non-defined medium incorporating tryptose, yeast extract, maltose and supplemented with 10% horse serum.

In in vitro drug studies, plant extracts are tested using a 96-well plate assay as described by Meingassner et al., (1978, *Antimicrob Agents Chemother* 13, 1–3). This method uses only 200 ul of medium/well and thus uses very little plant extract. Results (in triplicate) are presented as "Minimal Inhibitory Concentration" (MIC) the lowest concentration completely blocking growth (Meingassner et al., 1978, supra). This method is also useful in comparing susceptibility of various strains (Meingassner et al., 1978, supra; Yarlett et al., 1987, *Mol Biochem Parasitol* 24, 255–261). Assays will initially be done aerobically, but highly active compounds will also be tested anaerobically, since metronidazole resistance is only detectable under aerobic assay conditions (Meingassner et al., 1978, supra). Resistance to metronidazole is proposed to be due to the presence of defective oxygen scavenging mechanisms and resulting redox cycling of the partly reduced drug (Yarlett et al., 1986, *Mol Biochem Parasitol* 19, 111–116). Since vaginal O2 tensions are ½0th to ¼th of atmospheric (Wagner et al., 1978, *Fertil Steril* 30, 50–53), it is more physiological to do drug sensitivity testing under conditions approaching this.

(b) IN VIVO: Extracts or highly purified material proving active in vitro (MIC 0.5 mg/ml) with favorable selectivity will also be tested in vivo in a mouse subcutaneous infection model which has been used to correlate virulence of *T. vaginalis* isolates with severity of pathogenicity in the human host (Honigberg et al., 1966, Acta Cytol 10, 353–361; Kulda et al., 1970, *Am J Obstet Gynecol* 108, 908–918). This model has been used successfully to test various agents for trichomonacidal activity and is considered superior to other in vivo tests (Brenner et al., 1987; Kulda, 1989, *Trichomonads Parasitic in Humans*. Springer-Verlag, New York, pp 112–154).

EXAMPLE 1

Nineteen plant extracts were examined for activity in vitro against four strains of animal or human- pathogenic African trypanosomes, and three strains of mammalian-pathogenic Trichomonas spp..

The trypanosomes studied were *Trypanosoma brucei* brucei Lab 110 EATRO, which is pathogenic to cattle and other livestock, and several strains of *Trypanosoma brucei rhodesiense*, a parasite of humans, domestic and wild animals. Strains of *T. b. rhodesiense* included drug resistant clinical isolates KETRI 243 and 269 and KETRI 243 As-10-3, a highly melarsen- and diamidine-resistant clone of KETRI 243. The 19 extracts were tested in an in vitro screen using a semi-defined medium for growth of bloodstream trypomastigotes at 37° C. (Hirumi & Hirumi, 1989, supra) to determine $IC_{50}$ values (Bacchi et al., 1996, supra). Using a cutoff of 100 ug/ml, 12 of the 19 extracts consistently gave $IC_{50}$ values in the active range (Table 1). Of these, 10 had $IC_{50}$ values at or below 10 ug/ml and were considered sufficiently active to warrant testing of more purified extracts.

TABLE 1

Activity of plant extracts vs growth of African trypanosomes in vitro. Bloodform trypanosomes were grown in 24 well culture dishes (1 ml/well) in HMI-18 medium (Hirumi & Hirumi, 1989, supra). One half of the culture volume was replaced daily with fresh medium plus drug. Each extract was dissolved in 100% DMSO and diluted with medium. Cells were counted daily with a coulter counter. Data are as $IC_{50}$ values in ug extract/ml culture. Four strains were used: *T.b. brucei* Lab 110 EATRO, and three *T.b. rhodesiense* clinical isolates from the Kenya Trypanosomiasis Research Institute (KETRI). All data from 48 hr cultures. Control cell counts averaged $5 \times 10^6$ cell/ml at 48 h.

| | $IC_{50}$ (ug/ml) | | | |
|---|---|---|---|---|
| | EATRO 110 | KETRI 243 | KETRI 269 | KETRI 243 As-103 |
| SU-367 | 9.2 | 15.1 | 8.4 | 8.5 |
| SU-369 | 11 | 5.1 | 8.2 | 11 |
| SU-370 | 64 | 5 | 500 ug/ml-22% | 500 ug/ml-22% |
| SU-766 | 102 | 21.5 | 500 ug/ml-22% | 47 |
| SU-787 | 9.0 | 8.5 | 12.5 | 14.9 |
| SU-813 | 500 ug/ml-38% | 500 ug/ml-14% | 500 ug/ml-44% | 500 ug/ml-22% |
| SU-614 | 134 | 74 | 79 | 51 |
| SU-105 | 500 ug/ml-16% | 500 ug/ml-8% | 500 ug/ml-7% | 500 ug/ml-8% |
| SU-719 | 1.9 | 2.0 | 1.6 | 3.4 |
| SU-679 | 18.0 | 19.5 | 28.9 | 40.5 |
| SU-799 | 115 | 229 | 114 | 117 |
| SU-740 | 33 | 32.5 | 30.0 | 39.0 |
| SU-175 | 6.5 | 5.4 | 6.8 | 6.2 |
| SU-847 | 13.5 | 8.3 | 12.5 | 12.6 |
| SU-848 | 14.1 | 16.0 | 18.0 | 15.1 |
| SU-769 | 119 | 73.0 | 74 | 78 |
| SU-724 | 6.4 | 64.0 | 59 | 105 |
| Pentamidine | 0.00048 | 0.00186 | 0.00192 | 0.003 |
| Melarsen Oxide | 0.00077 | 0.0025 | 0.0066 | 0.0072 |

Several secondary extracts were recently shipped and tested (Table 2), while others are being prepared. Of the four secondary extracts supplied, one, SU1460, derived from the primary extract SU787 of Aframomum aulocacarpus, featured a 10–15 fold increase in activity. SU787 had IC50 values of 8.5–14.9 ug/ml (Table 1), while the value for SU1460 was 0.86 ug/ml.

TABLE 2

Activity of Secondary Plant Extracts on African Trypanosomes. Assay method as in Table 1. Results as $IC_{50}$ in ug/ml.

| Primary Extract | Origin | Secondary Extract | $IC_{50}$ T.b. brucei 110 |
|---|---|---|---|
| SU-724 | *Araliopsis tabouensis* AT6 | SU-1459 | 500* |
| SU-724 | *Araliopsis tabouensis* AT7 | SU-1458 | 100* |
| SU-787 | *Aframomum aulocacarpus* $AZ_2$ | SU-1460 | 0.86 |
| SU-175 | *Dracaena mannii* Mannispirostan A | SU-1461 | 6.4 |

*extracts precipitated in medium after 24 h.

Eight additional primary extracts were also tested in the trypanosome screen (Table 3). Of these, SU1462 from Napoleonaea imperialis and SU1464 from Glossocalyx brevipes were highly active ($IC_{50}$~1 ug/ml) and warrant further study.

TABLE 3

Growth inhibitory activity of new primary plant extracts against african Trypanosomes. Assay method as in Table 1. Results as $IC_{50}$ in ug/ml.

| Extract | Origin | $IC_{50}$ T.b. brucei 110 |
|---|---|---|
| SU 1462 | Napoleonaea imperialis MeOH | 1.75 |
| SU 1463 | Pachypodanthium staudtii $CH_2Cl_2$ | 88 |
| SU 1464 | Glossocalyx brevipes $CH_2Cl_2$ | 0.77 |
| SU 1465 | Enantia chlorantha MeOH | 10.5 |
| SU 1465 | Eupatorium odoratum MeOH EOO | 30% @ 50 ug/ml* |
| SU 1467 | Cleistopholis patens EtOH | 62 |
| SU 1468 | Leidobotrys staudii $CH_2Cl_2$ | |
| SU 1469 | Ancistrocladus bateri ABSBM | 28 |

*extract precipitates in medium at higher concentrations

The trichomonad screen consists of two human pathogenic *Trichomonas vaginalis* strains and a livestock parasite Tritrichomonas foetus. The *T. vaginalis* isolates include a metronidazole sensitive isolate (C1-NIH: ATCC 30001) and a strain highly resistant to metronidazole (CDC-085: ATCC 50143). The screening procedure used is that of Meingassner et al. (1978, supra) and determines the minimal inhibitory concentration (MIC) in mg/ml needed to completely inhibit growth. Table 4 details data from the initial group of 19 primary extracts. Of these, seven had MIC values of 1 mg/ml for all three isolates and were considered of interest for further study. The results to Dec. 31, 1997 appear in Table 5. The most active extract in this group was SU1464 from *Glossocalyx brevipes* which had an MIC value of 0.0125 mg/ml for each isolate and was the most potent of the primary extracts tested thus far.

TABLE 4

Minimum inhibitory concentration (mg/ml) of plant extracts against *Trichomonas vaginalis* strain C1-NIH (ATCC #30001) susceptible to current drug therapy (metronidazole and CDC-085 (ATCC#50143) resistant to metronidazole therapy; and the cattle parasite *Tritrichomonas foetus* KV-1. Assays were performed in 200 ul multiwell plates (96 well) by serial dilution of each compound (2.5 to 0.0012 mg/ml final concentration) and inoculated with 6.6 × 104 cells. Plates were scored after 48 h according to motility (4 = 100%, 0 = no motility) compared to control wells lacking the test compound (Meingassner et al., 1978, supra).

| | MIC (mg/ml) | | |
|---|---|---|---|
| ICBG# | C1-HIH 48 hrs | CDC-085 48 hrs | KV-1 48 hrs |
| SU-105 | >2.50 | 2.50 | >2.50 |
| SU-175 | 2.50 | 2.50 | 2.50 |
| SU-367 | 12.50 | 12.50 | 0.78 |
| SU-369 | 0.62 | 1.25 | 1.25 |
| SU-370 | 2.50 | 2.50 | 2.50 |
| SU-614 | 1.25 | 0.62 | 1.25 |
| SU-679 | 0.62 | 0.62 | 0.62 |
| SU-719 | 0.31 | 0.01 | 0.15 |
| SU-724 | 0.62 | 0.62 | 2.50 |
| SU-740 | 1.25 | 1.25 | 1.25 |
| SU-766 | 1.25 | 1.25 | 2.50 |
| SU-769 | 0.31 | 0.62 | 0.62 |
| SU-787 | 0.62 | 1.25 | 2.50 |
| SU-798 | 1.25 | 0.62 | 1.25 |
| SU-799 | 0.15 | 0.31 | 0.62 |
| SU-813 | >2.50 | >2.50 | 0.15 |
| SU-846 | 2.50 | 1.25 | 2.50 |
| SU-847 | >2.50 | >2.50 | >2.50 |
| SU-848 | 2.50 | 2.50 | 2.50 |
| Metronidazole | 0.003 | 0.40 | 0.004 |

TABLE 5

Inhibition of Trichomonas growth by new plant extracts. Assay method as in Table 4. Data expressed as MIC in mg/ml. ND, not determined.

| | | MIC | | |
|---|---|---|---|---|
| Extract | Origin | C1-NIH | CDC-085 | KV1 |
| SU 1463 | Pachypodanthium staudtii $CH_2Cl_2$ | 0.80 | ND | >0.80 |
| SU 1464 | Glossocalyx brevipes $CH_2Cl_2$ | 0.0125 | 0.0125 | 0.0125 |
| SU 1465 | Enantia chlorantha MeOH | 0.80 | ND | 0.40 |
| SU 1467 | Cleistopholis patens EtOH | >0.80 | 0.10 | >0.80 |
| SU 1468 | Leidobotrys staudii $CH_2Cl_2$ | 0.40 | ND | >0.80 |
| SU 1469 | Ancistrocladus bateri ABSBM | 0.40 | ND | 0.40 |
| Metronidaxole | | 0.003 | 0.40 | 0.003 |

The most active primary plant extracts in each screen are listed in Table 6. These were chosen on the basis of MIC levels (<1 mg/ml) for trichomonad screens and $IC_{50}$ values (</ =10 ug/ml) for trypanosomal screens. Although many of the extracts were most active only against one group of organisms, six primary extracts had significant activity against both groups. These were SU369, 719, 724, 787, 1464 and 1465. Of these, SU719 and 1464 appeared to be most potent in both screens.

TABLE 6

Most active: ICBG primary plant extracts.

| Trichomonas (MIC < 1 mg/ml) | Trypanosomes ($IC_{50}$ ≦ 10 ug/ml) | |
|---|---|---|
| SU-369+ | SU-175** | |
| SU-679* | SU-367 | |
| SU-719*+ | SU-369+ | |
| SU-724+ | SU-719**+ | |
| SU-769* | SU-724+ | |
| SU-787+ | SU-787**+ | |
| SU-799* | SU-798** | |
| SU-1464*+ | SU-846 | SU-1462 |
| SU-1465+ | SU-847 | SU-1464**+ |
| SU-1469 | SU-848 | SU-1465+ |

Although large-scale testing of plant extracts for activity against protozoan parasites is largely lacking (Wright & Phillipson, 1990, *Phytotherapy Res* 4, 127–139) recent evaluation of African medicinal plants vs. *T. b. rhodesiense* has given some encouraging results (Freiburghaus et al. 1996a, *J Ethnopharmacol* 55, 1–11; 1996b, *Trop Med Int Health* 1, 765–771; 1997, *Acta Tropica* 66, 79–83). In these studies crude extracts were considered to have promising activity in an in vitro screen against blood forms if $IC_{50}$ values were at or below 10 ug/ml. In the above trypanosome screen 13 of 27 primary medicinal plant extracts had such activity while two (SU719 and 1464) had $IC_{50}$ values at or below 1 ug/ml. Further studies will need to examine the selectivity of active extracts, i.e. the maximum tolerated concentrations by mammalian cell lines vs. the $IC_{50}$ or MIC values. If the selectivity data is favorable, further purification of the active principles and animal testing would be the logical next steps in the exploration of these extracts.

EXAMPLE 2

Using the leishmanial in vitro radiorespirometric bioassay the active compound was purified and its structure determined. A related species, Aframomum meleguata, showed moderate activity against Trypanosoma brucei in vitro $IC_{50}$ 9.0 ug/ml. However, a third plant species, *Aframomum aulocacarpus,* showed activity within the highly active drug range, $IC_{50}$ 0.86 ug/ml, a 10–11-fold increase in activity. The structural modifications in active antiparasitic with these botanical species changes are in progress.

EXAMPLE 3

Numerous similarities in leishmanial and trypanosomal lipid uptake and metabolism may explain common natural product drug susceptibility. Inhibitory of cholesterol synthesis, metabolism, and/or excretion described above in the detailed description were tested versus trypanosome isolates grown as bloodforms in HMI-18 medium containing 10% fetal bovine serum. Coulter counds were made daily and IC50 values determined after 48 h. Results are shown in Table 7.

TABLE 7

Drug compounds tested vs trypanosome isolates.

| | $IC_{50}$ (ug/ml) | | | |
|---|---|---|---|---|
| | Lab 110 EATRO | 243 | 269 | 243 As 10-3 |
| General inhibitors | | | | |
| Atromid-S | >100 | >100 | — | — |
| Lopoid | >100 | >100 | — | — |
| Bile Acid resorption inhibitors | | | | |
| Cholestipol | >100 | >100 | — | — |
| Questran | >100 | >100 | — | — |
| HMG-CoA reductase inhibitors | | | | |
| Baycol | 13 | 7.7 | — | 52 |
| Mevacor | 3.3 | 4.4 | 6.9 | — |
| Pravachol | >100 | >100 | — | — |
| Zocor | 1.33 | 12.9 | 7.0 | — |
| Lescol | >100 | >100 | — | — |
| Hormone agonists/antagonists | | | | |
| Tamoxifen | 30 | | | |

TABLE 7-continued

Drug compounds tested vs trypanosome isolates.

| | $IC_{50}$ (ug/ml) | | | |
|---|---|---|---|---|
| | Lab 110 EATRO | 243 | 269 | 243 As 10-3 |
| Citrate* | | | | |
| Tamoxifen* | 27 | | | |
| Squalene oxidase inhibitors | | | | |
| Lamisil | 1.3 | 86 | 77 | >100 |
| Thyroid hormone antagonists | | | | |
| Choloxin | >100 | >100 | — | — |

*uM

EXAMPLE 4

Targeted Anti-lipid Antileishmanials for Specialized Testing in Primates.

Two compounds selected as inhibitors of cholesterol synthesis and/or metabolism, and/or excretion will be tested at 3 dose levels in monkeys for evaluation against both monkey cutaneous and monkey visceral leishmaniasis. In 4 experiments we want to test 2-drug-combinations (4 combinations) as antileishmanials. The combinations we propose are already given in combination (for nonleishmanial indications) to humans. These drug combinations studies are in progress:

Positive control drug (Glucantime-treated) animals:(IP administration)
  dose 1–13 mg/kg/day (MKD)
  dose 2–52 mg/kg/day
  dose 3–104 mg/kg/day
Negative control (suspending drug vehicle-HEC tween minus drug): (IP administration)
PO administration:
  Drug 1 dose 1 (*human dose MKD level)
  Drug 1 dose 2 (10× human dose MKD level)
  Drug 1 dose 3: (100× human dose MKD level)
  Drug 2 dose 1 (*human dose MKD level)
  Drug 2 dose 2 (10× human dose MKD level)
  Drug 2 dose 3: (100× human dose MKD level)
  Drug 1 dose 1+drug 2 dose 1
  Drug 1 dose 2+drug 2 dose 1
  Drug 1 dose 3+drug 2 dose 1
  Drug 1 dose 1+drug 2 dose 2
  Drug 1 dose 2+drug 2 dose 2
  Drug 1 dose 3+drug 2 dose 2
  Drug 1 dose 1+drug 2 dose 3
  Drug 1 dose 2+drug 2 dose 3
  Drug 1 dose 3+drug 2 dose 3
  Candidate drugs 1 & 2 Vehicle Control (corn oil)
  *Dose will vary depending on the drug being tested.

DISCUSSION

Cholesterol is a sterol regulating the membrane fluidity of eukaryotic membranes (Stryer, 1988, *Biochemistry*. WH Freeman and Company, New York). Cholesterol contains a bulky steroidal nucleus with a hydroxyl group at one end and a flexible hydrocarbon tail at the other end (FIGS. 12–29, Stryer, 1988, supra). Cholesterol inserts into membrane lipid bilayers so that the hydrocarbon tail is located in the nonpolar core with the hydroxyl group bound to a carbonyl oxygen atom of a phospholipid polar head group oriented toward the aqueous exterior or interior of the cell (model previous page). The interaction forces between sterol molecules seem to be little affected by the double bond in the ring system or modifications in the side chain. Also, the change in orientation of the hydroxyl group from 3-beta to 3-alpha does not significantly alter the cross-sectional area of the sterol at the surface. However, replacement of the hydroxyl group by an oxogroup, or changes in the planar structure of the sterol nucleus, increase the molecular area, and may lead to some degree of membrane destabilization. This is why certain dimerized natural product plant components have antiparasite properties. Cholesterol prevents the crystallization of fatty acid chains by fitting between them. Thus, high concentrations of cholesterol tend to abolish phase transitions of lipid bilayers (Bloch, 1983, *CRC Critical Reviews in Biochemistry* 14, 47–92). Cholesterol (and sterol)—mediated stabilization from phase transitions of lipid bilayers is undoubtedly critical to the survival of Kintoplastida parasites which must undergo marked temperature transition from ambient (within the insect vector) to mammalian body temperature (37° C. or greater, dependent on reservoir or human mammalian host) during their life cycle. Dependent on Tm, melting temperature, fatty acid acyl chains in bilayers can exist either a more rigid or ordered state favoring trans C—C bonds; or, at rising temperature, a more disordered or gauche C—C bond conformation (a 120-degree rotation, clockwise, g+, or counterclockwise, g–) increases. The transition temperature, Tm, depends upon the length of the fatty acyl chains and amount of unsaturation. Saturated fatty acids result in an elevated Tm (e.g. Crisco shortening, a solid at room temperature) whereas, greater unsaturation increases fluidity (e.g. vegetable oils, liquid at room temperature) lowering Tm. Likewise, cholesterol prevents rigidity (crystalization) by fitting in between fatty acids increasing fluidity, so that at high membrane cholesterol concentrations, phase transition of bilayers are largely abolished. An opposite effect of cholesterol is to sterically block large motions of fatty acyl chains, making membranes less fluid. Membrane fluidity, i.e. cholesterol content therefore, and indeed sterol content in general, has strigent biologic control for each cell type/function (Thompson, 1992, *The Regulation of Membrane Lipid Metabolism,* CRC Press, Ann Arbor).

Medicinal herbs are of considerable importance to the health of individuals and communities worldwide. Even in industrialized countries, an estimated 33% of the population use alternative treatments including herbal remedies. Approximately 35,000 to 70,000 plant species have been used for medical purposes (Zhang, 1996, *World Health* 49*th year* (2) :4–5). Given the extraordinary ratio (approaching 50%) of "active to total screened" plants developed from our ICBG ethnomedical and ethnobotanical "leads" for antiparasitics, one must be impressed by the accuracy of the traditional healers' information. The fact that in the United States, two thirds of the drugs currently available on the market are originally based on medicinal plants then becomes somewhat less astounding (Micozzi, 1996, World Health 49th year (2):8–9). Most current antimalarials and other trypanosomals have their chemical origins in herbal extracts, thus, scientific history would lead one to believe that our ICBG approach is scientifically justified. The data presented in this disclosure support the that conclusion that the herbal extracts which, in fact chemically resemble various components of sterol biosynthesis and metabolism, act by inhibition of this pathway. The marked antiparasite efficacy of the known anticholesterol, antihyperlipidemics, cholesterol hormone antagonists, and anticancer drugs affecting this pathway for 3 of the four human parasite genera we have studied to date, not only provides immediate new chemotherapy for these infections in man and animals, but supports the concept that efficacious and nontoxic therapy for these diseases will be based on compounds affecting this pathway.

What is claimed is:

1. A method for treating an individual with a protozoan infection comprising administering to said individual a cholesterol synthesis inhibitor in a pharmaceutically effective amount, in a pharmaceutically effective excipient.

2. A method according to claim 1 wherein said administration is selected from the group consisting of oral, topical and parenteral.

3. A method as recited in claim 1, wherein said individual is a human.

4. A method for treating an individual with a protozoan infection comprising administering to said individual a cholesterol metabolism inhibitor in a pharmaceutically effective amount, in a pharmaceutically effective excipient.

5. A method according to claim 4 wherein said administration is selected from the group consisting of oral, topical and parenteral.

6. A method according to claim 4 where said individual is a human.

7. A method for treating an individual with a protozoan infection comprising administering to said individual a cholesterol excretion inhibitor in a pharmaceutically effective amount, in a pharmaceutically effective excipient.

8. A method according to claim 7 wherein said administration is selected from the group consisting of oral, topical and parenteral.

9. A method as recited in claim 7, wherein said individual is a human.

10. A method for preventing a protozoan infection in an animal comprising administering to said animal a cholesterol synthesis inhibitor in a pharmaceutically effective amount, in a pharmaceutically effective excipient.

11. A method according to claim 10 wherein said administration is selected from the group consisting of oral, topical and parenteral.

12. A method as recited in claim 10, wherein said animal is a human.

13. A method for preventing a protozoan infection in an animal comprising administering to said animal a cholesterol metabolism inhibitor in a pharmaceutically effective amount, in a pharmaceutically effective excipient.

14. A method according to claim 13 wherein said administration is selected from the group consisting of oral, topical and parenteral.

15. A method according to claim 3 where said animal is a human.

16. A method for preventing a protozoan infection in an animal comprising administering to said animal a cholesterol excretion inhibitor in a pharmaceutically effective amount, in a pharmaceutically effective excipient.

17. A method according to claim 16 wherein said administration is selected from the group consisting of oral, topical and parenteral.

18. A method as recited in claim 16, wherein said animal is a human.

* * * * *

UNITED STATES PATENT AND TRADEMARK OFFICE
CERTIFICATE OF CORRECTION

PATENT NO.    : 6,403,576 B1                                                    Page 1 of 1
DATED         : June 11, 2002
INVENTOR(S)   : Joan E. Jackson, Maurice M. Iwu, Christopher O. Okunji, Cyrus Bacchi,
                John D. Tally, Jr. and Johnson F. Ayafor It is certified that error appears in the above-identified patent and that said Letters Patent is hereby corrected as shown below:

<u>Title page,</u>
Item [73], the Assignee should be changed from "The United States of America as represented by the Secretary of the Navy" to -- The United States of America as represented by the Secretary of the Army, --

Item [75], the name of the fifth listed inventor should be changed from
"John D. Talley, Jr." to -- John D. Tally, Jr., --

Item [54], the title of the issued patent should be changed from "ANTIFUNGAL AND ANTIPARASITIC COMPOUNDS" to -- METHOD FOR TREATING AND PREVENTING PROTOZOAN INFECTIONS --

Signed and Sealed this

Twenty-second Day of October, 2002

*Attest:*

*Attesting Officer*

JAMES E. ROGAN
*Director of the United States Patent and Trademark Office*